United States Patent
Li et al.

(10) Patent No.: US 9,750,718 B2
(45) Date of Patent: Sep. 5, 2017

(54) METHODS OF TREATING HEPATIC FIBROSIS AND ASSOCIATED DISEASES BY REGULATING REV-ERB ACTIVITY

(71) Applicant: The Charlotte-Mecklenburg Hospital Authority, Charlotte, NC (US)

(72) Inventors: Ting Li, Charlotte, NC (US); Laura Schrum, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 14/651,413

(22) PCT Filed: Dec. 12, 2013

(86) PCT No.: PCT/US2013/074816
§ 371 (c)(1),
(2) Date: Jun. 11, 2015

(87) PCT Pub. No.: WO2014/093711
PCT Pub. Date: Jun. 19, 2014

(65) Prior Publication Data
US 2015/0328186 A1 Nov. 19, 2015

Related U.S. Application Data

(60) Provisional application No. 61/736,307, filed on Dec. 12, 2012.

(51) Int. Cl.
*A61K 31/381* (2006.01)
*A61K 31/4025* (2006.01)
(Continued)

(52) U.S. Cl.
CPC ........ *A61K 31/4025* (2013.01); *A61K 9/0014* (2013.01); *A61K 9/0019* (2013.01);
(Continued)

(58) Field of Classification Search
CPC .............. A61K 2300/00; A61K 31/381; A61K 31/4025; A61K 31/7105; A61K 45/06; A61K 47/48092; A61K 47/48284; A61K 47/48346
See application file for complete search history.

(56) References Cited

U.S. PATENT DOCUMENTS

2009/0280167 A1* 11/2009 Trieu .................... C12N 15/111
424/450

FOREIGN PATENT DOCUMENTS

| WO | 2011022619 A1 | 2/2011 |
| WO | 2013033310 A1 | 3/2013 |
| WO | 2013045519 A1 | 4/2013 |

OTHER PUBLICATIONS

Alzheimer's disease Mayoclinic [online] retrieved from: http://www.mayoclinic.com/health/alzheimersdisease/DS00161; Jan. 2013; 15 pages.).*

(Continued)

*Primary Examiner* — Ernst V Arnold
(74) *Attorney, Agent, or Firm* — Erin C. Wills; Smith Moore Leatherwood LLP

(57) ABSTRACT

The present invention is directed to compositions and associated methods for treatment, prevention, amelioration, and/or delaying the onset of hepatic fibrosis and/or associated diseases. The methods preferably involve regulating at least one of Rev-erbα expression, activity, and subcellular localization. In particular, certain embodiments of the present invention relate to compositions and methods of using a Rev-erb-modulating agent (REMA) for the treatment or prevention of hepatic fibrosis and/or associated diseases. Preferably, the amount of a REMA administered comprises a quantity sufficient to modulate at least one of Rev-erbα expression, activity, and subcellular localization and reduce the activation of hepatic stellate cells (HSCs).

28 Claims, 9 Drawing Sheets

(51) Int. Cl.
A61K 45/06 (2006.01)
A61K 47/48 (2006.01)
A61K 9/00 (2006.01)

(52) U.S. Cl.
CPC .......... *A61K 9/0053* (2013.01); *A61K 31/381* (2013.01); *A61K 45/06* (2013.01); *A61K 47/48092* (2013.01); *A61K 47/48284* (2013.01)

(56) References Cited

OTHER PUBLICATIONS

Wilson's Disease [online] retrieved from: https://medlineplus.gov/ency/article/000785.htm; 2016; 6 pages.).*
Bataller et al. (Journal of Clinical Investigation 2005;115(2):209-218).*
Marjolijn et al. (Pharm. Res. 2011;28:2045-2054).*
Lakner et al. (Hepatology Jul. 2012;56(1):300-310).*
Fontaine et al. (JBC 2003,278(39):37672-37680).*
Notification of Transmittal of the International Search Report and the Written Opinion for corresponding PCT Application No. PCT/US2013/074816, mailed Feb. 19, 2014, 13 pages.
Laura A. Solt et al., "Regulation of circadian behaviour and metabolism by synthetic REV-ERB agonists", Nature 11030, vol. 485, No. 7396, Mar. 29, 2012, pp. 62-68.
Naresh Kumar et al., "Regulation of Adipogenesis by Natural and Synthetic REV-ERB Ligands", Endocrinology, vol. 151, No. 7, Jul. 1, 2010, 18 pages.
T. Li et al., "Functional Role of REV-ERB in Modulation of Hepatic Stellate Cell Transdifferentiation", Journal of Hepatology, vol. 56, 2012, p. S152.

* cited by examiner

METHODS OF TREATING HEPATIC FIBROSIS AND ASSOCIATED DISEASES BY REGULATING REV-ERB ACTIVITY

The present application claims priority to U.S. Provisional Application No. 61/736,307, filed Dec. 12, 2012, the entire contents of which are incorporated herein by reference.

FIELD OF THE INVENTION

The present invention is directed to compositions and associated methods for the treatment, prevention, amelioration and/or delaying the onset of hepatic fibrosis and/or associated diseases, preferably by regulating one or more of Rev-erbα expression, activity, or subcellular localization. In particular, certain embodiments of the present invention relate to compositions and methods of using a Rev-erb-modulating agent (REMA) for the treatment, prevention, amelioration and/or delaying the onset of hepatic fibrosis and/or associated diseases.

BACKGROUND OF THE INVENTION

Hepatic fibrosis, the accumulation of abnormal extracellular matrix (ECM) proteins and a resultant loss of liver function, is an accompaniment of an inflammation-driven wound healing process triggered by chronic liver injury. Some of the main causes of liver injury leading to fibrosis include chronic hepatitis C virus (HCV) infection, alcohol abuse, chronic hepatitis B (HBV) infection, iron overload as occurs in hereditary hemochromatosis, drug induced liver injury (DILI), and increasingly non-alcoholic steatohepatitis (NASH) and non-alcoholic fatty liver disease (NAFLD).

Fibrosis of the liver is characterized by excessive deposition of ECM components, predominately type I collagen. Cytokine signaling predominates during fibrogenesis, serving to initiate activation of resident immune and hepatic stellate cells (HSCs) promoting wound repair. Activated HSCs are the principal cell type promoting synthesis and deposition of ECM proteins in response to increased levels of circulating inflammatory signals derived from damaged parenchymal cells. These resident vitamin A storing cells are found within the perisinusoidal space of Disse in a quiescent state, but upon hepatic injury the HSCs transdifferentiate into myofibroblast-like cells marked by expression of smooth muscle α-actin (αSMA), loss of retinyl ester stores, and increased proliferation and contractility. Myofibroblastic HSCs respond to and secrete a variety of profibrogenic cytokines including connective tissue growth factor (CTGF), tissue inhibitor of metalloproteinases, and transforming growth factor-beta (TGFβ). Of these, TGFβ has been recognized as the most potent fibrogenic cytokine regulating collagen production in HSCs via autocrine and paracrine signaling pathways.

The inflammatory process ensuing from hepatic injury triggers a variety of cellular responses including cell repair, hepatocyte regeneration, increased ECM turnover, and ultimately in some patients significant fibrosis. Disproportionate deposition of fibrillar collagens disrupts normal liver architecture and hepatic function and, if left untreated, may progress to cirrhosis and hepatocelluar carcinoma. Cirrhosis is a significant cause of morbidity and mortality worldwide. Accordingly there is an urgent need for antifibrotic therapies designed to impede and/or reverse fibrogenesis. See, e.g., Friedman (2010), Nat. Rev. Gastroenterol. Hepatol. 7:425-436.

BRIEF SUMMARY OF THE INVENTION

One or more embodiments of the present invention may address one or more of the aforementioned problems. Certain embodiments according to the present invention provide methods for treating, preventing, ameliorating, and/or delaying the onset of hepatic fibrosis and/or related pathologies. The hepatic fibrosis can be a symptom of one or more diseases and/or conditions, such as viral hepatitis, autoimmune hepatitis, drug induced liver injury (DILI), alcoholism, a metabolic disorder, or parasitic infection. In certain embodiments, the fibrosis is a symptom of a disease and/or condition other than non-alcoholic fatty liver disease (NAFLD), non-alcoholic steatohepatitis (NASH), obesity, a metabolic disease, and autoimmune hepatitis.

In certain embodiments, the methods comprise administering a composition comprising a therapeutically effective amount of one or more Rev-erb-modulating agents (REMA) to a mammal. The REMA can at least partially, directly or indirectly modulate (e.g., upregulate or downregulate) at least one of Rev-erbα expression, activity, or subcellular localization in at least a portion of the mammal's hepatic stellate cells (HSCs). In certain preferred embodiments, the composition includes an amount of at least one REMA sufficient to modulate (e.g., upregulate or downregulate) at least one of Rev-erbα expression, activity, or localization and reduce HSC activation. In certain embodiments, the REMA can at least partially, directly or indirectly, modulate (e.g., upregulate or downregulate) the expression, activity, or subcellular localization of at least one Rev-erb other than Rev-erbα (e.g., Rev-erbβ) in at least a portion of the mammal's hepatic stellate cells (HSCs).

The REMA can comprise a variety of forms, e.g., synthetic/natural ligand (e.g., small molecule ligand), enzyme, protein, nucleic acid, etc. In certain embodiments, the REMA is a compound selected from the group consisting of SR6452, SR9009, and SR9011. The REMA can be linked to a carrier/targeting moiety, such as mannose-6-phosphate modified human serum albumin. The carrier/targeting moiety can, for example, increase the serum half-life of the REMA and/or selectively deliver the REMA to HSCs.

In certain embodiments, the composition comprising a REMA can be administered along with at least one non-REMA therapeutic agent. The non-REMA therapeutic agent can be administered as part of the same composition or administered separately. In certain embodiments, the non-REMA therapeutic agent is selected from the group consisting of anti-viral agents, anti-fibrotic agents, immunomodulatory agents, cellular therapy (e.g., stem cells) and/or agents that suppress HSC activation. In certain embodiments, the non-REMA therapeutic agent is a miRNA, e.g., miR-19b.

In another aspect, the present invention provides a wide range of pharmaceutical compositions useful for treating, preventing, ameliorating and/or delaying the onset of hepatic fibrosis and/or related pathologies in a mammal, such as a human. In accordance with certain embodiments, the pharmaceutical compositions can comprise a therapeutically effective amount of one or more REMAs (optionally linked to a carrier/targeting moiety) and at least one pharmaceutically acceptable carrier. In other embodiments, the pharmaceutical composition can comprise a mixture of one or more REMAs and one or more non-REMA therapeutic agents (e.g., an anti-viral agent, an anti-fibrotic agent, an immunomodulatory agent, a cellular agent such as stem cells, or an agent that suppresses HSC activation). The pharmaceutical compositions can be formulated for administration to a mammal (e.g., a human) by various routes.

BRIEF DESCRIPTION OF THE DRAWINGS

Having described the invention in general terms, reference will now be made to the accompanying drawings.

FIG. 2A shows the results from freshly isolated primary rat HSCs that were culture-activated through day 4 in the presence of MDIR (a pro-adipogenic mixture) or embedded in matrigel. FIG. 2A also shows results from LX-2 cells (a human HSC cell line) that were embedded in matrigel for 72 hrs. FIG. 2B shows the results from primary HSCs that were treated with pro-fibrogenic factor TGFβ (5 ng/ml) or myosin inhibitors blebbistatin (Bleb) or BDM (2,3-Butanedione monoxime) for 48 hrs. Cells were harvested for protein and Western blots were performed to detect Rev-erbα.

FIG. 3A provides a chart summarizing the amount of PPARγ, SREBP1, and Lep mRNA detected after 5 days of culture. On day 15, cells were stained with Oil Red O as an indicator of adipogenesis, and the results are shown in FIG. 3B.

FIGS. 5A-D illustrate that Rev-erb agonist SR6452 can regulate myofibroblast marker expression and HSC contraction. Primary rat HSCs were cultured from quiescence (day Q) to day 5 (FIG. 5A) or from day 9 to day 12 (FIG. 5B) and treated with Rev-erb agonist SR6452. qRT-PCR was performed to detect myofibroblast gene expression. Samples were normalized with 18S rRNA. FIG. 5C shows results in which HSCs (day 9) were treated with DMSO or SR6452 for 72 hrs and immunocytochemistry was performed for αSMA (red fluorescence) and 4',6-diamidino-2-phenylindole (DAPI) (blue fluorescence). FIG. 5D shows HSCs (day 5) that were embedded in a collagen gel and treated as indicated for 48 hrs. Gels were released from their plastic surface and contraction monitored after 72 hrs. Materials used were DMSO, vehicle control; SR6452, Rev-erb agonist; and BDM (2,3-Butanedione monoxime), myosin inhibitor.

DETAILED DESCRIPTION OF THE INVENTION

Figure 1A:
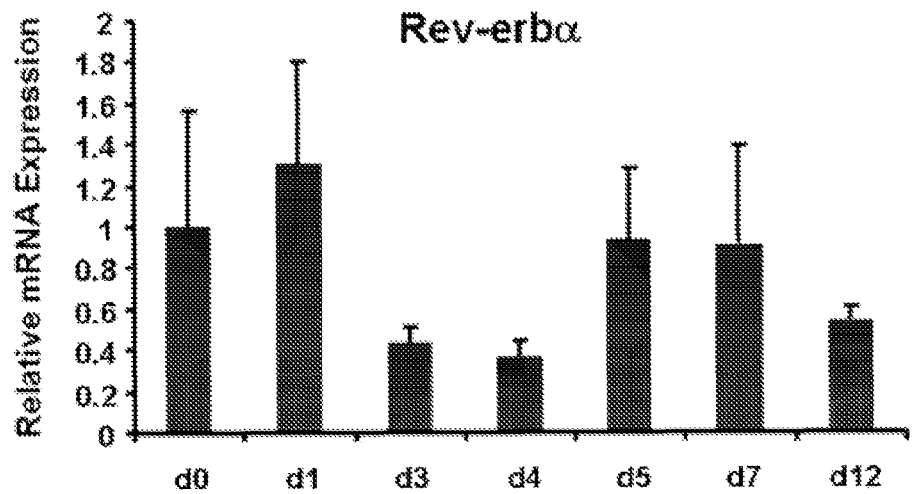
FIGS. 1A-1C illustrate modulation of Rev-erbα expression during HSC transdifferentiation. Primary rat HSCs were isolated and culture-activated through day (d) 20. Freshly isolated cells were considered quiescent (dQ). Cells were harvested for total RNA (FIGS. 1A and 1B) or protein (FIG. 1C), and qRT-PCR or Western blots were performed to detect Rev-erbα mRNA or protein expression, respectively. Pai-1 (FIG. 1B) and αSMA (FIG. 1C) were used as positive controls for HSC culture-activation.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Increased synthesis and deposition of type I collagen by activated HSCs is ultimately a major cause of organ dysfunction as a result of liver injury. In the normal/healthy liver, HSCs reside in a quiescent state, functioning to store vitamin A, modulating microcirculation, and regulating extracellular matrix (ECM) production. Following injury, HSCs transdifferentiate into an activated myofibroblast-like cell characterized by loss of vitamin A droplets, changes in cytoskeletal protein expression, including smooth muscle α-actin (αSMA), and hyper-contractility leading to decreased sinusoidal blood flow. Initiation of HSC activation is concomitant with the presence of several inflammatory and immunomodulatory molecules. The increased contractility associated with activation of HSCs leads to an undesirable increase in scarring of the liver, which can ultimately lead to liver fibrosis.

In one aspect, the present invention provides methods for treating, preventing, reversing, ameliorating and/or delaying the onset of hepatic fibrosis and/or related pathologies. Pathologies related to hepatic fibrosis include, e.g., cirrhosis, hepatocellular carcinoma (HCC), and neuronal and cardiovascular diseases. Generally, hepatic fibrosis is considered a symptom of another underlying condition or illness. Common conditions that give rise to hepatic fibrosis include chronic viral hepatitis (e.g., caused by HCV, HBV, etc.), autoimmune hepatitis, chronic alcoholism, drug induced liver injury (DILI) (e.g., caused by prescription drugs, non-prescription drugs, or toxins), non-alcoholic fatty liver disease (NAFLD), non-alcoholoic steatohepatitis (NASH), bile duct disease, a genetic diseases (e.g., hemochromatosis, glycogen storage disease, alpha-1 antitrypsin deficiency, Wilson disease, cystic fibrosis, primary sclerlosing cholanitis), malnutrition, cardiac problems, and parasitic infection (e.g., Schistosomiasis infection). In certain embodiments, the cause of the hepatic fibrosis is a condition other than NAFLD, NASH, obesity, a metabolic disease and/or autoimmune hepatitis. In certain embodiments, the cause of the hepatic fibrosis is DILI (e.g., caused by a drug overdose or a drug administered as part of a clinical trial).

In the liver, various fibrogenic mediators stimulate the activation and proliferation of collagen-producing cells, including HSCs. Without intending to be bound by theory, it is believed that such fibrogenic mediators influence the expression, activity and sub-cellular location of Rev-erbs, such as Rev-erbα and Rev-erbβ. For example, cytoplasmic Rev-erbs appear to be profibrotic, while nuclear Rev-erbs appears to help maintain the adipogenic or quiescent phenotype. At least some fibrogenic mediators appear to stabilize cytoplasmic Rev-erbα, thereby stimulating the activation of HSCs.

Accordingly, in certain embodiments of the present invention, the methods of the invention involve the treatment of cells (e.g., collagen-producing cells) or a mammal suffering from liver fibrosis by administering a therapeutically effective amount of one or more Rev-erb-modulating agents (REMA). In preferred embodiments, the composition includes an amount of at least one REMA sufficient to modulate (e.g., upregulate or downregulate) at least one of Rev-Erbα expression, activity, and subcellular localization and/or reduce HSC activation and contractility. In certain embodiments, the composition modulates at least one Rev-erb (e.g., Rev-erbα and/or Rev-erbβ by destabilizing cytoplasmic Rev-erb and stimulating nuclear localization, or vice versa. Modulation of the subcellular localization of Rev-erb (e.g., Rev-erbα and/or Rev-erbβ) according to certain embodiments of the present invention can beneficially impact HSCs. That is, the degree to which the HSCs are activated can be beneficially reduced.

Rev-erb Modulating Agents (REMAs)

Preferably, embodiments of the present invention utilize the administration of one or more REMAs to a mammal. In accordance with certain embodiments, the REMA is not particularly limited as long as the agent either directly or indirectly modulates (e.g., upregulates or downregulates) Rev-erbα expression, function, activity, and/or localization within HSCs. In certain embodiments, the REMA also modulates the expression, function, activity, and/or activity of Rev-erbβ within HSCs.

Rev-erbs are transcriptional repressors known to localize to the nucleus. As such, most studies have previously focused on its activity as a transcriptional factor. However, an increased cytoplasmic expression of Rev-erbα in activating or activated HSCs can also undesirably provide a fibrogenic function. Accordingly, certain embodiments of the present invention can comprise directly or indirectly modulating Rev-erbα cytoplasmic expression to at least partially mitigate the fibrogenic function associated with Rev-erbα cytoplasmic expression in HSCs.

Generally speaking, the term "REMA" as used herein, refer to compounds (e.g., small molecules, ligands, proteins, enzymes, antibodies, nucleic acids, etc.) that affect the activity of Rev-erbs in vivo and/or in vitro. REMAs can be agonists of Rev-erbs and can be compounds that exert their effect on Rev-erb activity via altering expression, via post-translational modifications, or by other means. Agonists of Rev-erbα can comprise molecules which, when bound to Rev-erbα, increase or prolong the activity of Rev-erbα (e.g., increase the nuclear localization and/or nuclear activity of Rev-erbα). Agonists of Rev-erbα according to certain embodiments of the present invention can include proteins, nucleic acids, carbohydrates, small molecules, or any other molecules which activate Rev-erbα. In certain embodiments, agonists of Rev-erbα also function as agonists of other Rev-erbs, such as Rev-erbβ, by increasing or prolonging the activity of the other Rev-erb (e.g., increasing the nuclear localization and/or nuclear activity of Rev-erbβ).

The term "modulate", as it appears herein, refers to a change in the activity or expression of a Rev-erb, such as Rev-erbα. For example, modulation may cause an increase or a decrease in protein activity, binding characteristics, or cellular localization, or any other biological, functional, or immunological properties of the Rev-erb.

In certain embodiments, the REMA can directly modulate Rev-erbα activity or expression in HSCs. In certain preferred embodiments, the REMA comprises a synthetic ligand (e.g., small molecule) that modulates Rev-erbα activity or expression. For instance, in certain embodiments, the REMA can comprise a synthetic agonist for Rev-erbα. Modulators of Rev-erbα activity and/or expression have been disclosed, e.g., in WO 2013/033310, the contents of which are incorporated herein by reference. Additional modulators of Rev-erbα activity can be identified by screening potential compounds, e.g., as described in Grant et al. (2010), ACS Chem. Biol. 5(10):925-32, the contents of which are incorporated herein by reference. Such potential compounds can include, for example, variants of any REMA compound specifically disclosed herein.

Exemplary synthetic agonists for Rev-erbs (e.g., Rev-erbα) include 1,1-Dimethylethyl N-[(4-chlorophenyl)methyl]-N-[(5-nitro-2-thienyl)methyl])glycinate; N-Benzyl-N-(4-chlorobenzyl)-1-(5-nitrothiophen-2-yl)methanamine; N-Benzyl-N-(3,4-dichlorobenzyl)-1-(5-nitrothiophen-2-yl) methanamine; 2-((4-chlorobenzyl)((5-nitrothiophen-2-yl)methyl)amino)-N,N-dimethylacetamide; or combinations thereof. Other exemplary synthetic agonists for Rev-erbs (e.g., Rev-erbα) include SR9009 and SR9011, which are described in WO 2013/033310 and are structurally related to the foregoing synthetic agonists. See, e.g., FIG. 1.

Certain embodiments of the present invention utilize the administration of synthetic Rev-erb agonist 1,1-Dimethyl-ethyl-N-[(4-chlorophenyl)methyl]-N-[(5-nitro-2-thienyl) methyl]) glycinate ($EC_{50}$=250 nM) or salt thereof, which is known as SR6452 or GSK4112 and is commercially available from Sigma Aldrich (USA). 1,1-Dimethylethyl-N-[(4-chlorophenyl)methyl]-N-[(5-nitro-2-thienyl)methyl])glycinate will hereinafter be referred to as "SR6452". Rev-erb agonist SR6452 enhances recruitment of nuclear receptor co-repressor (NCoR) peptide to Rev-erbα. The structure of SR6452 is as follows:

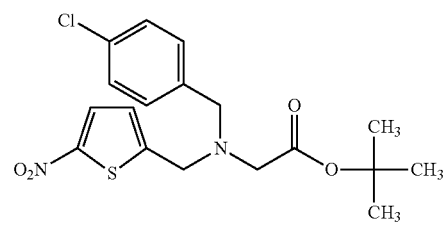 [SMILES: CC(C)(C)OC(=O)CN(Cc1ccc(Cl)cc1)Cc1ccc([N+](=O)[O-])s1]

In certain embodiments, the REMA can comprise N-Benzyl-N-(4-chlorobenzyl)-1-(5-nitrothiophen-2-yl)methanamine. The structure of N-Benzyl-N-(4-chlorobenzyl)-1-(5-nitrothiophen-2-yl)methanamine is as follows:

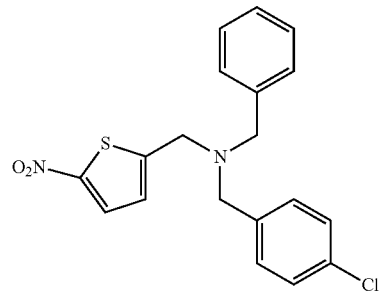 [SMILES: O=[N+]([O-])c1ccc(CN(Cc2ccccc2)Cc2ccc(Cl)cc2)s1]

In certain embodiments, the REMA can comprise N-Benzyl-N-(3,4-dichlorobenzyl)-1-(5-nitrothiophen-2-yl)methanamine. The structure of N-Benzyl-N-(3,4-dichlorobenzyl)-1-(5-nitrothiophen-2-yl)methanamine is as follows:

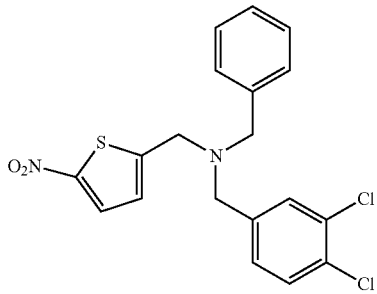 [SMILES: O=[N+]([O-])c1ccc(CN(Cc2ccccc2)Cc2ccc(Cl)c(Cl)c2)s1]

In certain embodiments, the REMA can comprise 2-((4-chlorobenzyl)((5-nitrothiophen-2-yl)methyl)amino)-N,N-dimethylacetamide. The structure of 2-((4-chlorobenzyl)((5-nitrothiophen-2-yl)methyl)amino)-N,N-dimethylacetamide is as follows:

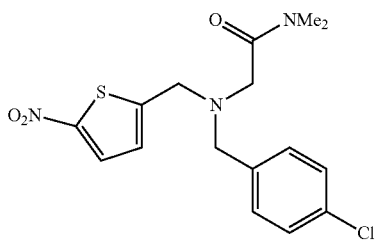 [SMILES: CN(C)C(=O)CN(Cc1ccc(Cl)cc1)Cc1ccc([N+](=O)[O-])s1]

In certain embodiments, the REMA is a compound related to SR6452, such as SR9009 or SR9011. See, e.g., WO 2013/033310.

In accordance with certain embodiments of the present invention, the REMA can comprise a natural molecule (e.g., Heme modulators). For instance, a natural REMA can include enzymes, antibodies, proteins, nucleic acids, carbohydrates, small molecules, or combination thereof including upstream regulators (both known such as GSK3β and/or novel).

To improve efficacy and/or reduce side effects, the REMA can be linked to another moiety that functions as a carrier and/or targeting moiety. Preferably, the other moiety selectively targets HSCs. Suitable targeting moieties include, e.g., mannose-6-phosphate modified human serum albumin. See, e.g., van Beuge et al. (2013), PLOS ONE 8(2): e56442, the contents of which are incorporated herein by reference. The carrier/targeting moiety can, in some embodiments, increase the serum half-life of the REMA. In other embodiments, the carrier/targeting moiety increases the serum half-life of the REMA and selectively targets HSCs.

As noted previously, REMAs according to certain embodiments of the present invention can indirectly modulate Rev-erbα activity or expression. In such embodiments, REMA preferably targets or interacts with a component of the HSC upstream to Rev-erbα expression or a component that regulates nuclear transport of Rev-erbα. This component, for instance, can then function to modulate Rev-erbα expression or activity. Accordingly, the REMA effectively modulates Rev-erbα activity or expression indirectly through interaction with the upstream component of the HSC that subsequently affects the activity or expression of Rev-erbα due to the initial interaction with the REMA. In certain such embodiments, the REMA can comprise enzymes, antibodies, proteins, nucleic acids, carbohydrates, small molecules, or combinations thereof. The component of the HSC upstream to Rev-erbα expression can comprise, for example, an enzyme, antibody, protein, nucleic acid, carbohydrate, or combinations thereof including upstream regulators (known regulators, such as GSK3β, and/or novel regulators).

Rev-erb

Rev-erb proteins are members of the nuclear receptor family of intracellular transcription factors. There are two forms of the receptor, alpha (α) and beta (β), each encoded by a separate gene (NR1D1 and NR1D2, respectively).

Rev-erbα, also known as NR1D1 (nuclear receptor subfamily 1, group D, member 1) is a transcriptional repressor. Rev-erbα is highly expressed in the liver, skeletal muscle, adipose tissue, and the brain, in mammals, participating in the development and circadian regulation of these tissues. Preitner N, et al., (2002). "The orphan nuclear receptor REV-ERBα controls circadian transcription within the positive limb of the mammalian circadian oscillator". Cell 110 (2): 251-60. doi:10.1016/S0092-8674(02)00825-5. PMID 12150932; Triqueneaux G, et al, (2004). "The orphan receptor Rev-erbα gene is a target of the circadian clock pacemaker". J. Mol. Endocrinol. 33 (3): 585-608. doi:10.1677/jme.1.01554. PMID 15591021. Gibbs, et al., 2009 Circadian Timing in the Lung; a Specific Role for Bronchiolar Epithelial Cells, Endocrinology 2009. 150:268-276. doi 10.1210/en.2008-0638. Rev-erbα regulates gene transcription by directly binding to target response elements (RevREs), comprises an A/T-rich flank followed by AGGTCA. Rev-erbα mediates repression by recruiting the corepressor N-CoR, which then activates the histone deacetylase (HDAC) 3.

Therapeutically Effective Amount

In accordance with certain embodiments of the present invention, a therapeutically effective amount of a REMA can generally comprise an amount sufficient to achieve its intended purpose. More specifically, a therapeutically effective amount can comprise an amount effective to prevent development of hepatic fibrosis or alleviate the existing symptoms, or revert activated HSCs back to a quiescent state in the subject being treated. A therapeutically effective amount can vary based on a range of factors (e.g., route of administration, patient's age, patient's weight, severity of disorder, etc.) and determination thereof is well within the capability of those skilled in the art.

For instance, a therapeutically effective amount of a REMA can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in mammals (e.g., humans).

A therapeutically effective amount of a REMA can also refer to that amount of the compound that results in amelioration of symptoms or a prolongation of survival in a patient. Toxicity and therapeutic efficacy of a REMA can be determined by standard pharmaceutical procedures in cell cultures or experimental animals (e.g., for determining the LD50—the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosages or amounts for use in mammals (e.g., humans). The dosage or amount of a REMA preferably lies within a range of circulating concentrations that include the ED50 with little or no toxicity. The dosage or amount may vary within this range depending upon the dosage form employed and the route of administration utilized. The exact formulation, route of administration and dosage can be chosen by the individual physician in view of the patient's condition. Dosage amount and interval may be adjusted individually to provide plasma levels of the active moiety which are sufficient to maintain the desired effects.

In cases of local administration or selective uptake, the effective local concentration of the REMA may not be related to plasma concentration.

The amount of REMA-containing composition administered can, of course, be dependent upon several factors including the subject being treated, on the subject's weight, the severity of the affliction, the manner of administration and the judgment of the prescribing physician.

In certain embodiments of the present invention, a REMA can be administered to a mammal having liver fibrosis or exhibiting symptoms of liver fibrosis in an amount sufficient to modulate Rev-erb (e.g., Rev-erbα) expression, activity, and/or subcellular location, impede activation of HSCs, and/or revert activated HSCs into a quiescent state. In accordance with certain embodiments, Rev-erb (e.g., Rev-erbα) expression and/or activity can be modulated by at least 1%, 5%, 10%, 15%, 20%, 25%, 30%, 35%, 40%, 45%, 50%, 55%, 60%, 65%, 70%, 75%, 80%, 85%, 90%, 95%, or more. For instance, Rev-erb expression and/or activity can be modulated from at least any of the following: 1%, 5%, 10%, 15%, 20%, 25%, 30%, 35%, 40%, 45%, 50%, 55%, 60%, 65%, 70%, 75%, 80%, 85%, 90%, 95%, and/or at most about any of the following 5%, 10%, 15%, 20%, 25%, 30%, 35%, 40%, 45%, 50%, 55%, 60%, 65%, 70%, 75%, 80%, 85%, 90%, 95%, 100% (e.g., 5-100%, 10-90%, 20-80%, etc.). In other embodiments, Rev-erb (e.g., Rev-erbα) subcellular localization can be modulated (e.g., shifted to the nucleus) by at least 1%, 5%, 10%, 15%, 20%, 25%, 30%, 35%, 40%, 45%, 50%, 55%, 60%, 65%, 70%, 75%, 80%, 85%, 90%, 95%, or more. For instance, Rev-erb (e.g., Rev-erbα) subcellular localization can be modulated (e.g., shifted to the nucleus) such that the amount of Rev-erb in a particular location (e.g., the nucleus) is from at least any of the following: 30%, 35%, 40%, 45%, 50%, 55%, 60%, 65%, 70%, 75%, 80%, 85%, 90%, 95%, to at most about any of the following 80%, 85%, 90%, 95%, 100% (e.g., 30-100%, 40-90%, 50-80%, etc.).

In certain embodiments, the methods can comprise the administration of a therapeutically effective amount of a REMA, in which the amount of the REMA comprises an amount sufficient to halt activation of HSCs, preferably concomitantly with modulation of Rev-erbα expression, activity, and/or subcellular location. For instance, the rate at with HSCs are activated can begin to reduce until no noticeable further activation of additional HSCs is realized. In this regard, these embodiments can provide a means to effectively impede or stop the further progression or severity of liver fibrosis and related pathologies.

In certain preferred embodiments, the methods can comprise the administration of a therapeutically effective amount of a REMA, in which the amount of the REMA comprises an amount sufficient to revert at least a portion of any activated HSCs into a quiescent phenotype, preferably concomitantly with an upregulation or overexpression of Rev-erbα. In such embodiments, the degree of scarring due to fibrosis can be reduced to beneficially reduce the consequences associated with liver fibrosis. That is, when activated hepatic stellate cells revert back into a quiescent phenotype (associated with healthy or normal HSCs) their degree of contractility reduces (e.g., the HSCs "relax" from a contracted state) and decreased expression of fibrogenic markers (e.g., collagen, smooth muscle α-actin). This "relaxation" of the HSCs and downregulation of fibrogenic markers can enhance the overall anti-fibrotic effects of manipulating Rev-erbα activity or expression.

In certain embodiments, for instance, the HSCs of a mammal exhibit an initial degree of contractility prior to administration of a REMA. The initial degree of contractility can be evaluated, for example, based on a measurement of the portal pressure gradient as is known in the art. After administration of a composition comprising a therapeutically effective amount of the REMA, the HSCs of the mammal exhibit a second degree of contractility that is less than the initial degree of contractility. Again, the second degree of contractility can be evaluated, for example, based on a measurement of the portal pressure gradient as is known in the art. In certain preferred embodiments, the second degree of contractility subsequent to administration of the REMA is sufficiently reduced in comparison to the initial degree of contractility such that at least a portion of the mammals liver sinusoids are at least partially relaxed. Traditionally, portal venous pressure is monitored, and HSC relaxation is not. Therefore, the treatment strategy according to certain embodiments of the present invention is novel, in at least one respect, since certain embodiments of the present invention are targeting HSC contractility rather than the consequence (i.e., portal hypertension) of increased HSC contraction.

The relaxed state of contractility realized after treatment according to certain embodiments of the present invention can be exhibited or realized at least once from 15 minutes to 24 hours from the time of administration (e.g., intravenously, orally, or in cell-culture). For instance, the second degree of contractility subsequent to administration of a REMA according to certain embodiments of the present invention can be exhibited or realized at least after any of 0.25, 0.5, 1.0, 2, 4, 6, 10, 12, and 18 hours after administration; and/or at most any of 8, 12, 15, 18, 24, 36, and 48 hours after administration (e.g., between 0.25-24 hours, 1-18 hours, 4-8 hours, etc. from the time of administration). In certain embodiments, the portal pressure gradient can be monitored continuously or in intervals to facilitate identification of a need for a second treatment, variance in dosage amount, and/or development of a treatment schedule for days or weeks.

In certain embodiments, the mammal (e.g., human) being treated has been diagnosed as having liver fibrosis. In other embodiments, however, the mammal (e.g., human) being treated may not technically have liver fibrosis but may be exhibiting symptoms similar to or associated with liver fibrosis. In certain embodiments, the mammal (e.g., human) being treated may be identified as being at risk of developing liver fibrosis in view of diagnosis of conditions known to ultimately lead to development of liver fibrosis (e.g., viral infection, chemical intake, etc.). In such embodiments, the administration of a REMA in accordance with certain embodiments of the present invention can beneficially facilitate or prevent development of liver fibrosis.

Methods according to certain embodiments of the present invention can comprise administering a therapeutically effective amount of a REMA to a patient in which the patient also suffers from at least one of hepatic cirrhosis, acute alcoholic hepatitis, schistosomiasis, primary biliary cirrhosis, acute and fulminant hepatitis, congenital hepatic fibrosis, peliosis hepatitis, veno-occlusive disease, Budd-Chiari syndrome, vitamin A toxicity, Sclerosing cholangitis, Hepatitis B, Hepatitis C, non-alcoholic steatophepatitis (NASH), non-alcoholic fatty liver disease (NAFLD), alcoholic liver disease, a metabolic liver disease, Wilson's disease, and hemochromatosis.

In certain embodiments of the present invention, the methods of treatment can comprise a combination therapy including a treatment method as described herein in combination with another treatment, such as traditional approaches for treating liver fibrosis or related pathologies, including diet, medications, endoscopic therapy, surgery, or radiology. In certain embodiments, methods of treatment can comprise administering a therapeutically effective amount of one or more REMAs to a patient concomitantly, serially, or in an alternating fashion (e.g., variable or fixed dosing regimens) with another therapeutic agent. The other therapeutic agent can be one that is designed to treat the underlying cause of the hepatic fibrosis, such as an anti-viral agent (e.g., an anti-HCV or anti-HBV agent). For example, the anti-viral agent can be ribavirin, peginterferon alpha-2a, boceprevir, telaprevir, raltegravir, entecavir, sofosbuvir, mericitabine, setrobuvir, declatasvir, ledipasvir, asunaprevir, faldaprevir, simeprevir, danoprevir, sovaprevir, miravirsen, VX-135, VX-222, ABT-267, ABT-333, BI207127, GS-5816, GS-9451, GS-9669, GSK2336805, ACH-3102, TMC647055, ACH-3102, MK-5172, MK-8742, IDX719, or any combination thereof. Alternatively, the other therapeutic agent can be one that is designed to treat hepatic fibrosis and/or inhibit activation of HSCs, such as miR-19b (see, e.g., US Application 2013/0053429, the content of which is incorporated herein by reference), an angiotensin II receptor antagonist (e.g., irbesartan, losartan, or candesartan), oltipraz, or GS-6624. Other therapeutic agents suitable for combination therapy include traditional medicaments for treating portal hypertension (e.g., vasodilators, nitric oxide, organic nitrates, adrenolytics, calcium channel blockers, and beta blockers).

In accordance with certain embodiments of the present invention, the pharmaceutical compositions can comprise a REMA in combination with a wide variety of pharmaceutically acceptable carriers or excipients. The particular carriers or excipients can be varied depending on various factors including route of administration, presence or absence of a carrier/targeting moiety, and desired delivery system (e.g., sustained release, timed-released, immediate release, selective release, etc.). For example, the composition can be made to suit the desired mode of administration. Pharmaceutically acceptable carriers can be determined, in part, by the particular composition being administered, as well as by the particular method used to administer the composition. Accordingly, there is a wide variety of suitable formulation recipes of pharmaceutical compositions containing one or more REMAs. For example, the pharmaceutical carrier may comprise a virus, a liposome (e.g., cationic lipids mixed with a REMA to form liposomes carrying the REMA), or a polymer (e.g., cationic polymers such as DEAE-dextran or polyethylenimine in which the REMA complexes with the polycation and the complex is taken up by the cell via endocytosis).

The administration of a pharmaceutical composition comprising a REMA may be carried out by known methods, wherein a desired molecule is introduced into a desired target cell in vitro or in vivo. In general, methods of administering small molecules, nucleic acids, enzymes and proteins are well known in the art. REMA compositions in accordance with certain embodiments of the present invention can be administered by a number of routes including, but not limited to: oral, intravenous, intraperitoneal, intraarterial, intramuscular, transdermal, subcutaneous, topical, sublingual, or rectal means. Alternatively, the REMA can be administered using a cellular vehicle, such as cells "loaded" with the REMA ex vivo.

Administration of the compositions described herein may be accomplished by any acceptable method which allows a REMA to reach its target. Any acceptable method known to one of ordinary skill in the art may be used to administer a composition to the subject. The administration may be localized (i.e., to a particular region, physiological system, tissue, organ, or cell type) or systemic, depending on the condition being treated. In certain embodiments, the targeted tissue comprises a HSC.

Injections can be, for example, intravenous, intradermal, subcutaneous, intramuscular, or intraperitoneal. In certain embodiments, the injections can be given at multiple locations if desired. In certain embodiments, the compositions can be delivered by implantation. Implantation can include inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. In certain embodiments, the compositions can be delivered by inhalation. Inhalation can include administering the composition with an aerosol in an inhaler, either alone or attached to a carrier that can be absorbed. For systemic administration, it may be preferred that the composition is encapsulated in liposomes.

Preferably, the REMA delivery systems are provided in a manner which enables tissue-specific uptake of the REMA. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

In certain embodiments according to embodiments of the present invention, a nucleic acid encoding a REMA molecule can be provided on a vector. Such vectors can include a sequence encoding a particular REMA of choice and in vivo expression elements. Vectors can include, but are not limited to, plasmids, cosmids, phagemids, viruses, other vehicles derived from viral or bacterial sources that have been manipulated by the insertion or incorporation of the nucleic acid sequences for producing the desired REMA, and free nucleic acid fragments which can be attached to these nucleic acid sequences. Viral and retroviral vectors are a preferred type of vector according to certain embodiments and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Ban viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have general utility for the high-efficiency transduction of nucleic acids in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N.J. (1991).

In certain embodiments, a therapeutically effective amount of one or more REMAs can be delivered to a mammal via a nanoparticle-based drug delivery system. Nanoparticle-based drug delivery systems can have considerable potential for treatment of liver fibrosis and/or related pathologies. For instance, nanoparticles used as carriers for REMAs can provide the benefits of high stability, high carrier capacity, feasibility of incorporation of both hydrophilic and hydrophobic substances, and feasibility of variable routes of administration, including oral application and inhalation. In certain embodiments, the nanoparticles can also be designed to allow controlled (sustained) release of the REMA from the matrix. The aforementioned properties of nanoparticles, according to certain embodiments of the present invention, can provide improvement of bioavailability and/or reduction of the dosing frequency. Nanoparticles for the purpose of REMA delivery can be defined as submicron (<1 μm) colloidal particles. The colloidal particles can include monolithic nanoparticles (nanospheres) in which the REMA is adsorbed, dissolved, or dispersed throughout the matrix and nanocapsules in which the REMA is confined to an aqueous or oily core surrounded by a shell-like wall. Alternatively, the REMAs can be covalently attached to the surface or into the matrix. Nanoparticles, according to certain embodiments of the present invention, can be made from biocompatible and biodegradable materials such as polymers, either natural (e.g., gelatin, albumin) or synthetic (e.g., polylactides, polyalkylcyanoacrylates), or solid lipids. In the body of the mammal being treated, the REMAs loaded in nanoparticles can be released from the matrix by a variety of mechanisms including, for example, diffusion, swelling, erosion, degradation, or combinations thereof.

In one embodiment, the composition comprising one or more REMAs can be perfused directly through the targeted tissue, such as the liver. For example, the composition containing a REMA can be perfused directly through a body organ (e.g., liver), without introducing the REMA into the body's general circulation, removing them from the organ with effluent blood and transporting the contaminated blood to an extracorporeal circuit where the blood is treated to remove the contamination, and returning the treated blood to the body. In some embodiments, such a process may help prevent undesirable levels of the REMA from entering the body's general circulation while delivering effective doses to the HSCs. Methods of perfusing active agents through a body organ, such as the liver, are described in greater detail in U.S. Pat. No. 5,069,662, the contents of which are incorporated by reference in their entirety.

In certain embodiments, the compositions can be delivered using a bioerodible implant by way of diffusion or by degradation of a polymeric matrix. In certain embodiments, the administration of the compositions may be designed so as to result in sequential exposures to the REMA over a certain time period, for example, hours, days, weeks, months or years. This may be accomplished, for example, by repeated administrations or by a sustained or controlled release delivery system in which a REMA is delivered over a prolonged period without repeated administrations. Administration of the compositions using such a delivery system may be, for example, by oral dosage forms (e.g., tablet, capsule, etc.), bolus injections, transdermal patches or subcutaneous implants. Maintaining a substantially constant concentration of the REMA may be preferred in some cases.

Other suitable delivery systems include, but are not limited to, time-release, delayed release, sustained release, or controlled release delivery systems (e.g., tablets, capsules, etc.). Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which a synthetic compound (e.g., SR6452, SR9009, SR9011) is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The compositions may be as, for example, microspheres, hydrogels, polymeric reservoirs, cholesterol matrices, or polymeric systems. In certain embodiments, the system may allow sustained or controlled release of the composition to occur, for example, through control of the diffusion or erosion/degradation rate of the formulation containing the REMA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose can be determined by the efficacy of the particular formulation, and the activity, stability or serum half-life of the REMA employed and the condition of the patient, as well as the body weight or surface area of the patient to be treated. The size of the dose can also be determined by the existence, nature, and extent of any adverse side-effects that accompany the administration of a particular composition in a particular patient.

Therapeutic compositions comprising one or more REMAs can optionally be tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the REMA at various concentrations, e.g., as applied to the mass and overall health of the patient. Administration can be accomplished via single or divided doses.

Compositions according to certain embodiments described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers.

EXAMPLES

Example 1: Involvement of Rev-erbα in HSC Transdifferentiation

A series of experiments were conducted to determine the functional role of Rev-erbα in HSC transdifferentiation. In these experiments, culture-activated primary rat HSCs and human LX-2 cells were used. To determine the effect of Rev-erbα on HSC transdifferentiation and contraction, cells were treated with a specific synthetic modulator, SR6452 (10 μM). mRNA and protein expression were determined by qRT-PCR and Western blot, respectively. Changes in cellular morphology, Rev-erb expression/localization and αSMA expression were observed by confocal microscopy. Additionally, cell contractility was assessed.

I. Materials and Methods

Primary Cell Isolation and Culture

Primary rat HSCs were isolated by pronase/collagenase perfusion digestion followed by density gradient centrifugation with Optiprep. Media was replaced every other day to replenish Rev-erbα modulator SR6452, which was present at a 10 μM concentration. Cells were treated with MDIR mixture (IBMX, dexamethasone, insulin, rosiglitazone), TGFβ, or DMSO (vehicle). Some experiments were performed with the human HSC cell line, LX-2.

Quantitative Real-Time PCR (qRT-PCR)

mRNA expression was normalized to 18S rRNA.

Immunocytochemistry

Prior to transfection, culture-activated HSCs (for varying days of activation) were seeded onto glass coverslips. Cells were fixed with 4% paraformaldehyde and stained with anti-αSMA antibody, a marker of HSC activation. Cells were imaged using a Zeiss confocal microscope. The fluorescence indicates Rev-erb or αSMA expression.

Cell Contraction Assay

Primary rat HSCs (day 9, $2\text{-}5\times10^6$ cells/ml) were embedded in a collagen lattice per manufacturer's instructions. Cells were treated with synthetic Rev-erbα ligand SR6452. Collagen gel size change was imaged using a BioSpectrum Imaging System.

Statistical Analysis

Data are presented as mean±SEM as determined from at least two independent experiments.

II. Results

Figure 1B:
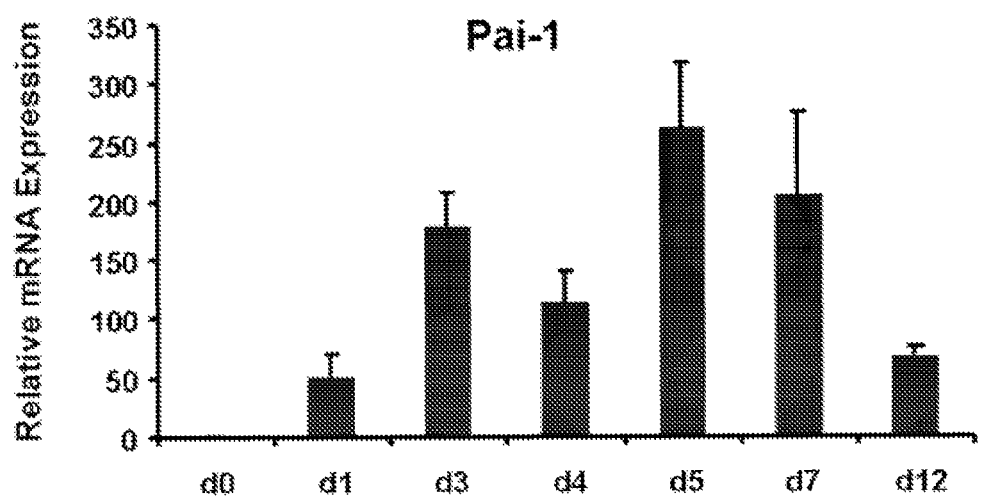
Figure 1C:
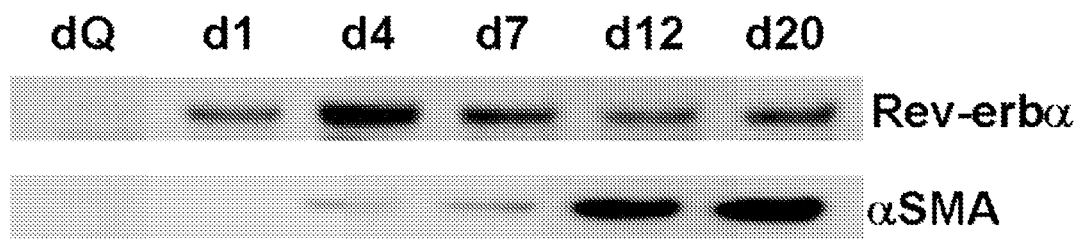

FIGS. 1A-1B show that Rev-erbα expression is modulated during HSC transdifferentiation. Primary rat HSCs were isolated and culture-activated through day (d) 20. Freshly isolated cells were considered quiescent (dQ). Cells were harvested for total RNA (FIGS. 1A and 1B) or protein (FIG. 1C) and qRT-PCR or Western blots were performed to detect Rev-erbα expression. Pai-1 (FIG. 1B) and αSMA (FIG. 1C) were used as positive controls for HSC culture-activation.

Figure 2A:
FIGS. 2A-B illustrate the regulation of Rev-erbα expression by pro- and anti-fibrogenic factors.
Figure 2B:
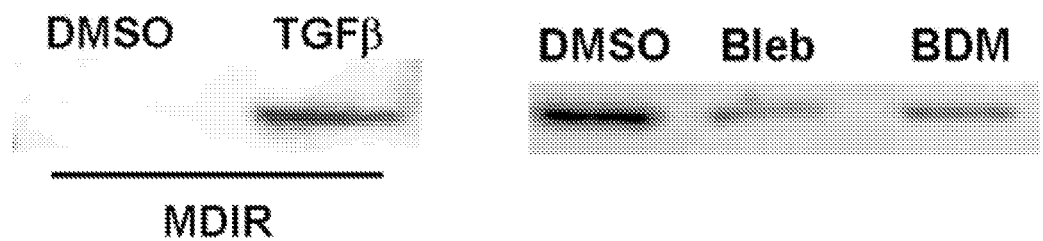

FIGS. 2A-B show that regulation of Rev-erbα expression can be controlled by both pro- and anti-fibrogenic factors. FIG. 2A shows results from freshly isolated primary rat HSCs that were culture-activated through day 4 in the presence of MDIR, a pro-adipogenic mixture, or embedded in matrigel. FIG. 2A also shows results from LX-2 cells that were embedded in matrigel for 72 hrs. FIG. 2B show results from primary HSCs that were treated with pro-fibrogenic factor TGFβ (5 ng/ml) or myosin inhibitors blebbistatin (Bleb) or BDM (2,3-Butanedione monoxime) for 48 hrs. Cells were harvested for protein and Western blots performed to detect Rev-erbα.

Figure 3A:
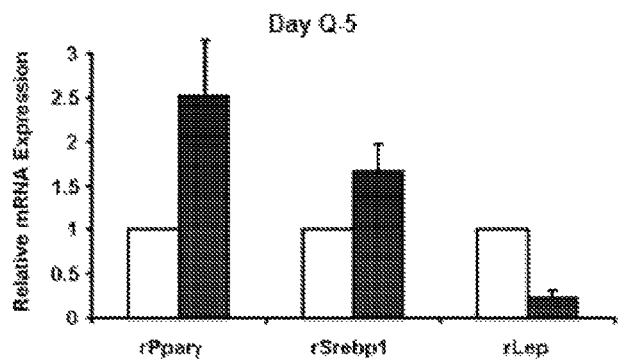
FIGS. 3A-B illustrate how modulation of Rev-erbα activity can regulate adipogenesis. Primary HSCs were culture-activated for 5 days (A) or 15 days (B). Cells were treated with vehicle, DMSO (open bar), or Rev-erb agonist SR6452 (10 μM, solid bar).
Figure 3B:
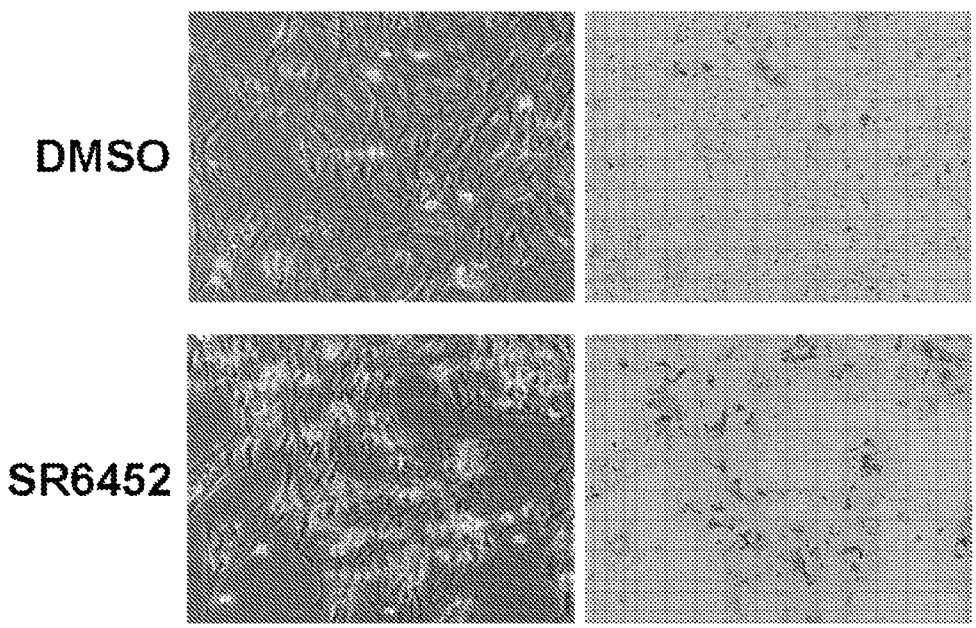

FIGS. 3A-B illustrates that modulation of Rev-erbα activity can regulate adipogenesis. Primary HSCs were culture-activated for 5 days (A) or 15 days (B). Cells were treated with vehicle (DMSO, open bar), or the Rev-erbα modulator SR6452 (10 mM, purple bar) for the days indicated. The medium was changed every 48 hrs. FIG. 3A provides a chart summarizing the amount of PPARγ, SREBP1, and Lep mRNA on day 5. On day 15, cells were stained with Oil Red O as an indicator of adipogenesis and the results are shown in FIG. 3B.

Figure 4A:
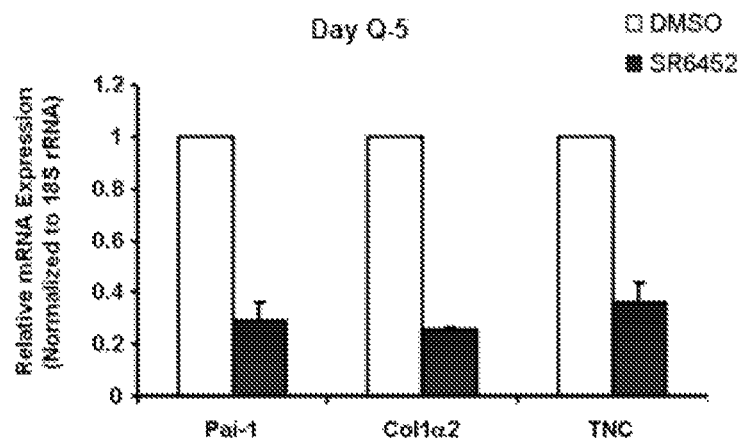
FIGS. 4A-B illustrate that the Rev-erb agonist SR6452 can suppress/decrease ECM gene expression. Primary rat HSCs were cultured with Rev-erb agonist SR6452 from quiescence (day Q) to day 5 (FIG. 4A) or from day 9 to day 12 (FIG. 4B) while being treated. qRT-PCR was performed to detect ECM gene expression. DMSO was used as the vehicle control.
Figure 4B:
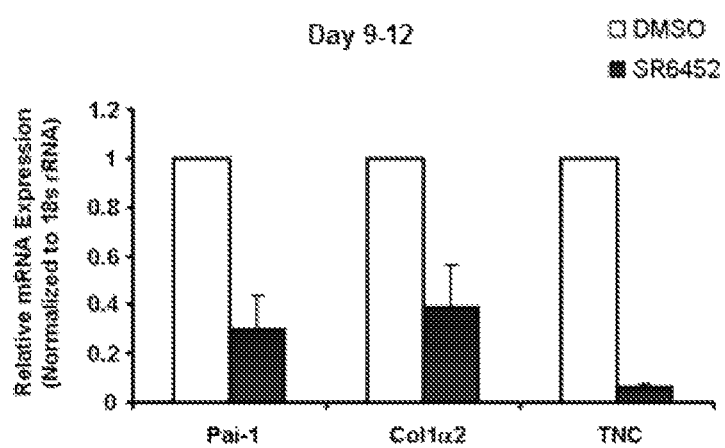
Figure 5A:
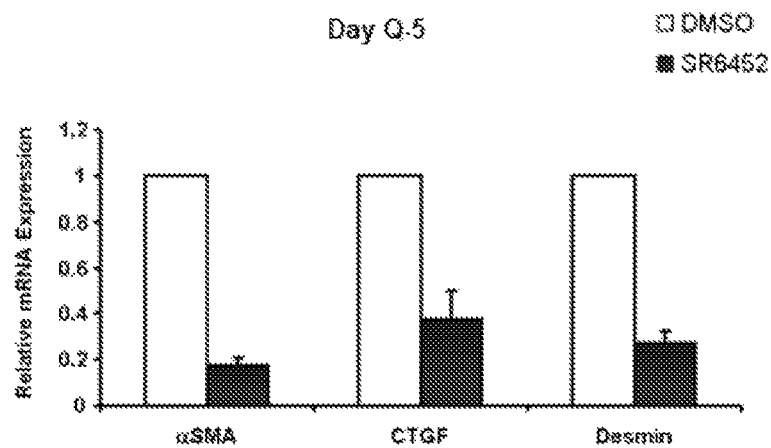
Figure 5B:
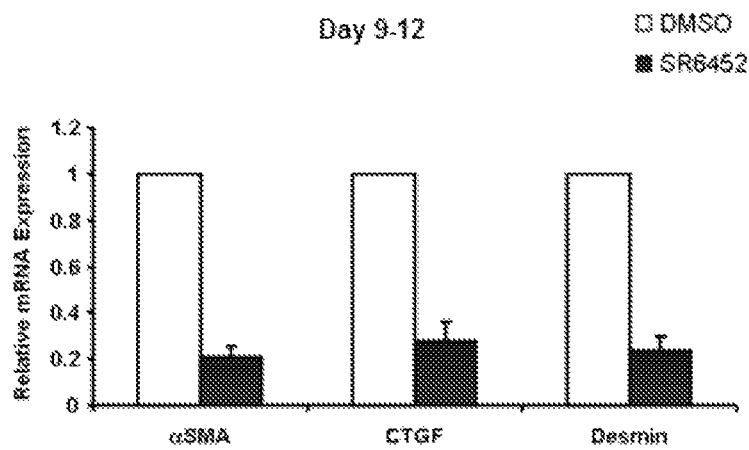

FIGS. 4A-B illustrate that the Rev-erbα modulator SR6452 can suppress/decrease ECM gene expression. Primary rat HSCs were cultured from quiescence (day Q) to day 5 (FIG. 4A) or from day 9 to day 12 (FIG. 4B) and treated with Rev-erbα modulator SR6452. qRT-PCR was performed to determine ECM gene expression. DMSO was used as the vehicle control, while SR6452 was used as the Rev-erbα modulator.

Figures 5C, 5D:
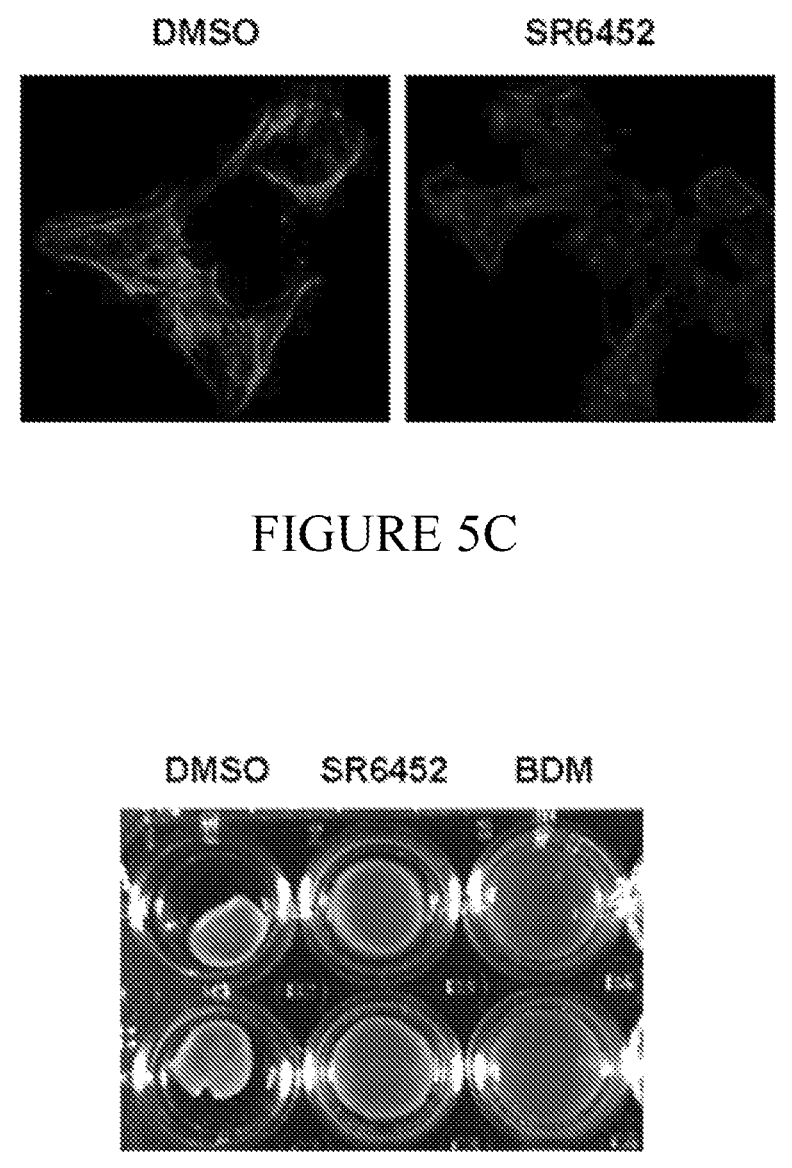

FIGS. 5A-D illustrate that Rev-erbα modulator SR6452 can regulate myofibroblast marker expression and HSC contraction. Primary rat HSCs were cultured from quiescence (day Q) to day 5 (FIG. 5A) or from day 9 to day 12 (FIG. 5B) and treated with Rev-erbα modulator SR6452.

qRT-PCR was performed for myofibroblast gene expression. Samples were normalized with 18S rRNA. FIG. 5C shows results in which HSCs (day 9) were treated with DMSO or SR6452 for 72 hrs and immunocytochemistry was performed for αSMA (red fluorescence) and 4',6-diamidino-2-phenylindole (DAPI) (blue fluorescence). HSCs (day 5) were embedded in a collagen gel and treated as indicated for 48 hrs. Gels were then released from plastic surface and contraction monitored after 72 hrs. Materials used were DMSO (vehicle control), SR6452, Rev-erb modulator; and BDM (2,3-Butanedione monoxime), myosin inhibitor.

III. Brief Summary of Results

The results above show that during in vitro HSC activation, Rev-erbα protein expression is increased. The presence of Rev-erbα modulator SR6452, in contrast, increased lipid content in activated HSCs and up-regulated expression of major adipogenic factors, notably PPARγ and SREBP1. SR6452 also significantly down-regulated expression of key extracellular matrix components, including Type I collagen, fibronectin, and tenascin C, concomitant with repressive effects on major regulatory and structural genes controlling myofibroblast contraction. Morphologically, SR6452-treated primary HSCs showed a slightly rounded/folded cytoplasm with disoriented actin fibers. Additionally, SR6452 impeded HSC contraction.

More specifically, the results shown in the figures and discussed above illustrate that expression of Rev-erbα mRNA and protein was modulated during HSC activation with peak protein expression on day 4. Regulation of Rev-erbα expression and subcellular localization was controlled by both pro- and anti-fibrotic factors. Matrigel or adipogenic mixture, MDIR, decreased Rev-erbα protein expression, while TGFβ increased expression and stabilized cytoplasmic Rev-erbα. Additionally, myosin inhibition decreased Rev-erbα protein expression. As can also be seen from the results above, exposure of quiescent HSCs to SR6452 promoted HSC adipogenesis.

These experiments illustrate that Rev-erbα expression during HSC activation inversely correlates with cellular adiposity. The data obtained with the Rev-erb specific modulator SR6452 indicates a suppressive effect of this compound on HSC activation, suggesting a functional role of Rev-erbα in maintaining/promoting the adipocyte phenotype while suppressing myofibroblast markers in HSCs.

Example 2: Control of HSC Activation by Rev-erbα

Activation of HSCs is a major contributor to hepatic fibrogenesis, a process characterized by accumulation of scar matrix, hepatic cell death and disruption of normal liver architecture. Therefore, experiments were conducted to determine if Rev-erbs play a role in controlling the process of HSC activation.

I. Methods

Primary rat HSCs were isolated via standard pronase-collagenase digestion and subsequent density gradient centrifugation. LX-2 cells were treated with adipogenic mixture (MDI), 5 ng/ml of recombinant transforming growth factor-beta (TGFβ), or plated on Matrigel™ (growth condition which promotes HSC quiescence) for various time points. Gene expression was determined by RealTime PCR and Western blot. Immunocytochemistry followed by confocal microscopy was used to determine sub-cellular localization. A Rev-erb DNA binding domain (DBD) mutant was produced by standard molecular cloning. LX-2 cells were transfected with expression vectors or controls using Fugene®HD.

II. Results

Using an in vitro model (primary rat cells) of HSC activation, upregulation of Rev-erbα was detected at the protein level, with immunocytochemistry demonstrating significant cytoplasmic accumulation. When stimulated with known adipogenic (MDI) and fibrogenic (TGFβ) compounds, expression patterns of Rev-erbα were analogous. Human HSCs (LX-2) manipulated to ectopically express recombinant Rev-erbα mirrored the results found in primary cells. Compared to control vector, forced expression of Rev-erbα potentiated TGFβ dependent activation of plasminogen activator inhibitor-1 and type I collagen. Overexpression of Rev-erbα conferred previously non-responsive LX-2 cells sensitive to Rev-erb agonist SR6452. Moreover, when cultured in Matrigel™, cells expressing a truncation mutant of Rev-erbα (known to localize to the cytoplasm) showed significantly higher smooth muscle alpha actin expression, supporting a fibrogenic functionality of cytoplasmic Rev-erbα.

III. Brief Summary of Results

Figure 6:
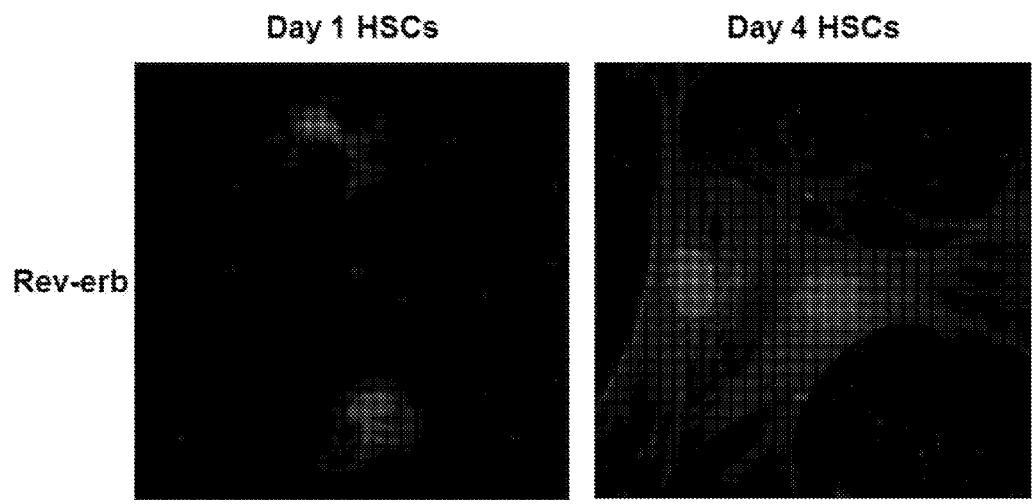
FIG. 6 illustrates nuclear and cytoplasmic expression of Rev-erbα in quiescent HSCs (day 1), and robust cytoplasmic expression of Rev-erbα in activating or activated HSCs (day 4 activated cells).
Figure 7:
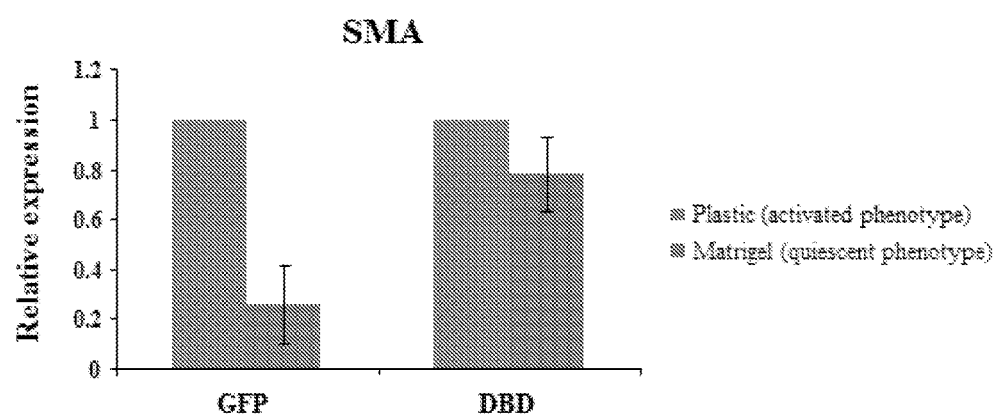
FIG. 7 shows a bar chart illustrating the relative expression of smooth muscle alpha actin (αSMA) in transformed LX-2 cells grown on plastic or matrigel. The cells were transformed with a control green fluorescent protein (GFP) or a truncation mutant of Rev-erbα (DBD) known to localize to the cytoplasm.

The results illustrate that upregulation and cytoplasmic accumulation of Rev-erbα are integral to both the myofibroblast phenotype and the fibrogenic response during HSC activation. Since Rev-erbs are transcriptional repressors known to localize to the nucleus, and most studies have focused on its activity as a transcriptional factor. However, these results illustrate the observation of a robust cytoplasmic expression of Rev-erbα in activating or activated HSCs (day 4 activated cells) compared to quiescent (day 1) as shown in FIG. 6. It was hypothesized that increased cytoplasmic expression has a fibrogenic function. To further investigate the possible contribution of the cytoplasmic accumulation of Rev-erbα to HSC activation a mutant form of Rev-erbα (DBD) that has a truncation from amino acid 1-235 was constructed in the lab. This mutant has been shown to localize to the cytoplasm due to loss of a nuclear localization signal in the DBD. When cultured in 3D Matrigel, which promotes HSC quiescence, LX-2 cells (a human myofibroblast cell line) expressing DBD showed higher mRNA expression of αSMA, a marker of HSC activation as shown in FIG. 7. These results confirm that cytoplasmic Rev-erbα includes a fibrogenic function.

Example 3: Inhibition of $CCl_4$-Induced Liver Fibrosis

The in vivo effects of the Rev-erb agonist SR9009 were tested using a mouse model for chemically induced liver fibrosis.

I. Materials and Methods

Male C57BL/6 mice (age 9 weeks) were injected intraperitoneally with carbon tetrachloride ($CCl_4$) in sterile olive oil (1 µl $CCl_4$/g body weight) twice a week for 5 weeks. Three weeks after initiation of $CCl_4$ treatment, SR9009 (EMD Millipore, dissolved in DMSO) was administered 5 times a week at a dose of 0.1 mg/g body weight for two weeks. Mice were sacrificed 72 hours after the last dose of SR9009 and livers were harvested for further analysis.

For histology studies, livers of the right and left lobes were fixed in 10% formalin, embedded in paraffin, sectioned, and stained with herovici to detect collagen deposition. For gene expression studies, total RNA was extracted from whole liver homogenates, and qRT-PCR performed to detect various markers, including αSMA, Col1α1, Col1α2, tenascin C, and connective tissue growth factor.

II. Results

Figure 8A:
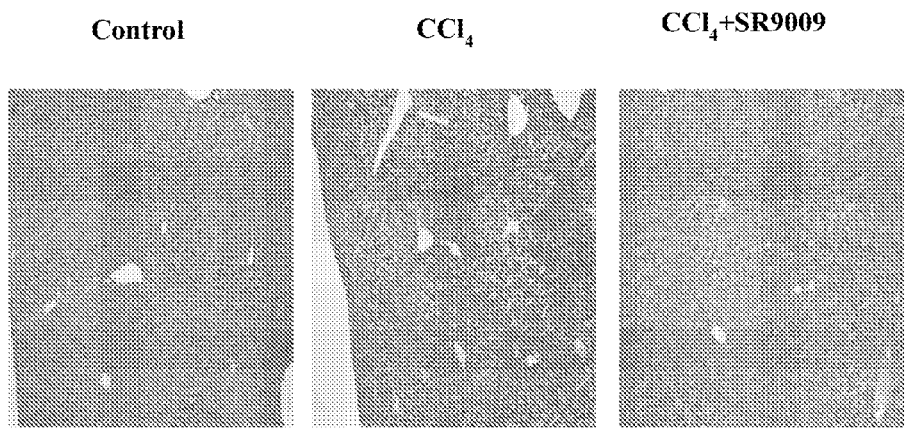
FIG. 8A depicts sectioned liver tissue that has been treated with a control vehicle, $CCl_4$, or $CCl_4$ and SR9009. The sections were stained with herovici to detect collagen deposition.

FIG. 8A depicts sectioned liver tissue and shows that $CCl_4$ treatment results in increased collagen deposition and disrupted liver architecture. Treatment with SR9009, however, reverses the effects of $CCl_4$ treatment, resulting in an essentially normal liver architecture and amount of collagen deposition.

Figure 8B:
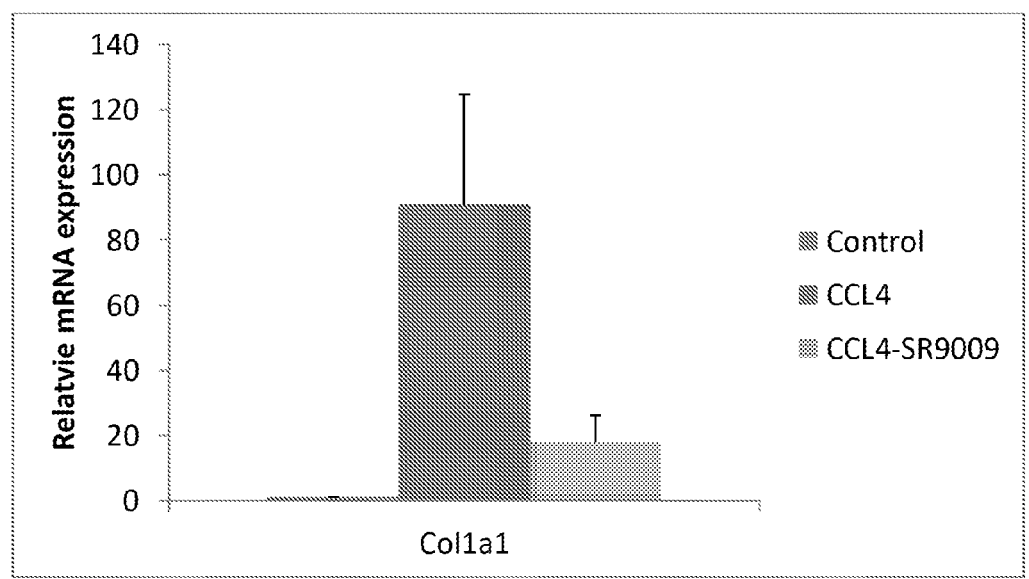
FIGS. 8B, 8C, and 8D are graphs depicting the expression of Col1α1, Col1α2, and αSMA, respectively, in mice treated with control vehicle, $CCl_4$, or $CCl_4$ and SR9009.
Figure 8C:
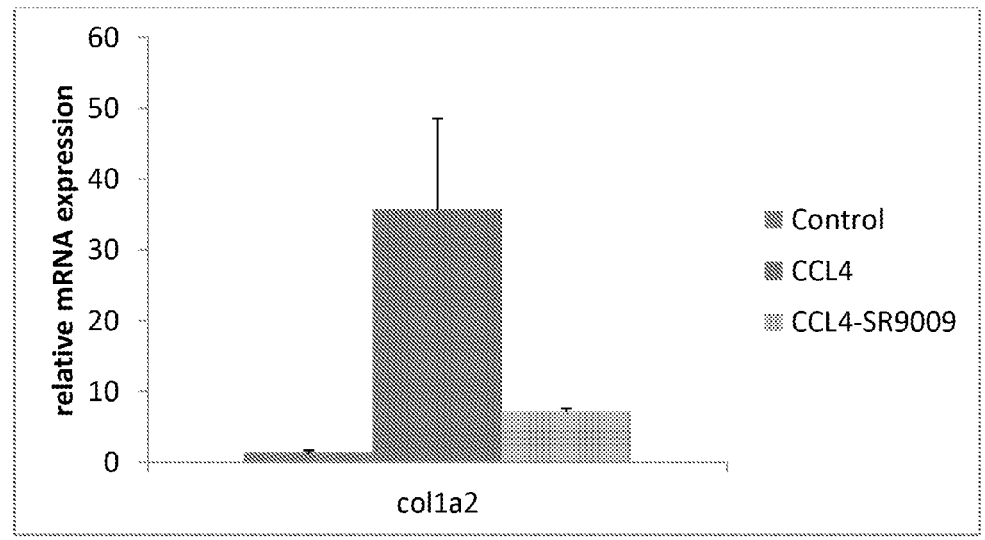
Figure 8D:
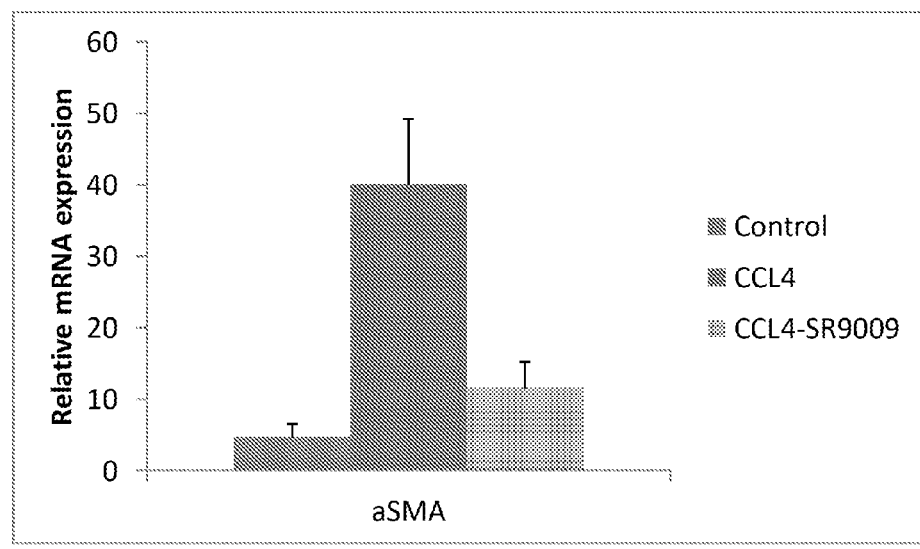

FIGS. 8B, 8C, and 8D are graphs that show that $CCl_4$ treatment stimulates increased expression of Col1α1, Col1α2, and αSMA, respectively. However, treatment with SR9009 dramatically reduces the $CCl_4$-induced increases in expression, bringing the expression levels of Col1α1, Col1α2, and αSMA down to almost normal levels. Similar results were observed for tenascin C and connective tissue growth factor (data not shown).

III. Brief Summary of Results

Based on the histological and expression data, SR9009 effective reverses $CCl_4$-mediated liver fibrosis in mice. This suggest that SR9009 and related REMAs can be used in humans to treat liver fibrosis, particularly fibrosis arising from DILI.

Example 4: Specific Targeting of REMAs to HSCs

Rev-erbα is expressed in cell types other than the HSCs involved in liver fibrosis, including hepatocytes. It is therefore desirable to limit the distribution of REMAs to activated HSCs. This can be done by linking the REMA to a suitable targeting moiety.

Accordingly, in this example, the REMA SR9009 is attached to mannose-6-phosphate human serum albumin (M6PHSA). The M6PHSA moiety binds to the insulin-like growth factor II receptor on activated HSCs, and has been shown to successfully target, e.g., a Rho kinase inhibitor and an ALK5 inhibitor to HSCs. See, e.g., van Beuge et al. (2013), PLOS ONE 8(2): e56442. The linkage between SR9009 and M6PHSA can be achieved using the Universal Linkage System (ULS™), as described. Id.

Many modifications and other embodiments of the invention set forth herein will come to mind to one skilled in the art to which these inventions pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating, ameliorating, or delaying the onset of liver fibrosis and related pathologies in a mammal in need thereof, the method comprising:
providing a composition comprising a therapeutically effective amount of one or more Rev-erb-modulating agents (REMAs), the one or more REMAs being selected from the group consisting of 1,1-Dimethylethyl N-[(4-chlorophenyl)methyl]-N-[(5-nitro-2-thienyl)methyl])glycinate; N-Benzyl-N-(4-chlorobenzyl)-1-(5-nitrothiophen-2-yl)methanamine; N-Benzyl-N-(3,4-dichlorobenzyl)-1-(5-nitrothiophen-2-yl) methanamine; 2-((4-chlorobenzyl)((5-nitrothiophen-2-yl)methyl)amino)-N,N-dimethylacetamide; SR9009; SR9011; and combinations thereof; and
administering the composition to the mammal, the therapeutically effective amount comprising a quantity sufficient to modulate at least one of Rev-erbα expression, activity, and subcellular localization in at least a portion of the mammal's hepatic stellate cells (HSCs),
wherein the one or more REMAs is contained in a vector selected from the group consisting of a plasmid, cosmid, phagemid, or virus.

2. The method of claim 1, wherein the one or more REMAs: modulates Rev-erbα activity or subcellular localization in at least a portion of the mammal's HSCs, increases Rev-erbα nuclear activity and/or nuclear localization, decreases Rev-erbα cytoplasmic activity and/or cytoplasmic localization, or combinations thereof.

3. The method of claim 1, wherein the modulation is direct.

4. The method of claim 1, wherein the one or more REMAs comprises at least one synthetic ligand or small molecule.

5. The method of claim 1, wherein the one or more REMAs comprises at least one natural REMA.

6. The method of claim 1, wherein the one or more REMAs comprises an enzyme, an antibody, a protein, or combination thereof.

7. The method of claim 1, wherein at least one of the one or more REMAs is linked to a carrier/targeting moiety.

8. The method of claim 7, wherein the carrier/targeting moiety is mannose-6-phosphate modified human serum albumin.

9. The method of claim 1, wherein the related pathologies comprise cirrhosis, HCC, neuronal diseases, cardiovascular diseases, or combinations thereof.

10. The method of claim 1, wherein a therapeutically effective amount of the one or more REMAs comprises an amount sufficient to halt activation of HSCs.

11. The method of claim 1, wherein a therapeutically effective amount of the one or more REMAs comprises an amount sufficient to revert at least a portion of any activated HSCs into a quiescent phenotype.

12. The method of claim 1, wherein the one or more REMAs modulates expression, activity, and/or subcellular localization of at least one Rev-erb in addition to Rev-erbα in at least a portion of the mammal's HSCs.

13. The method of claim 12, wherein the at least one Rev-erb in addition to Rev-erba is Rev-erbβ.

14. The method of claim 1, wherein the mammal also suffers from at least one of viral hepatitis, autoimmune hepatitis, hepatic cirrhosis, acute alcoholic hepatitis, schistosomiasis, primary biliary cirrhosis, acute and fulminant hepatitis, congenital hepatic fibrosis, peliosis hepatitis, veno-occlusive disease, Budd-Chiari syndrome, vitamin A toxicity, Sclerosing cholangitis, non-alcoholic steatohepatitis (NASH), non-alcoholic fatty liver disease (NAFLD), alcoholic liver disease, a metabolic liver disease, Wilson's disease, and hemochromatosis.

15. The method of claim 1, wherein the mammal does not suffer from non-alcoholic fatty liver disease (NAFLD), non-alcoholic steatophepatitis (NASH), obesity, a metabolic disease, or autoimmune hepatitis.

16. The method of claim 1, wherein Rev-Erba expression is modulated by at least 10%, 15%, 20%, 25%, 30%, 35%, 40%, 45%, 50%, 55%, 60%, 65%, 70%, 75%, 80%, 85%, 90%, 95%, or more, and/or Rev-erbα nuclear localization is increased to at least 10%, 15%, 20%, 25%, 30%, 35%, 40%, 45%, 50%, 55%, 60%, 65%, 70%, 75%, 80%, 85%, 90%, 95%, or more.

17. The method of claim 1, wherein the mammal is a human.

18. The method of claim 1, wherein the step of administering the composition comprises oral, intravenous, intraperitoneal, intramuscular, transdermal, subcutaneous, topical, or sublingual administration.

19. The method of claim 1, wherein the composition comprises a pharmaceutically acceptable carrier.

20. The method of claim 19, wherein the composition is provided in the form of a liquid injectable composition, tablet, capsule, liquid oral composition, loaded nanoparticle, or transdermal patch.

21. The method of claim 19, wherein the pharmaceutically acceptable carrier comprises a virus, liposome, polymer, or combinations thereof.

22. The method of claim 1, further comprising the step of perfusing the composition comprising the one or more REMAs through a targeted tissue of the mammal.

23. The method of claim 22, wherein the targeted tissue comprises at least a portion of the HSCs of the mammal.

24. The method of claim 1, further comprising administering a non-REMA therapeutic agent either at the same time or at a different time as administering the composition comprising the one or more REMAs, wherein the non-REMA therapeutic agent is an anti-viral agent, miR-19b, an angiotensin II receptor antagonist, or a vasodilating medicament.

25. A pharmaceutical composition, comprising: a therapeutically effective amount of one or more Rev-erb-modulating agents (REMA) and at least one pharmaceutically acceptable carrier, wherein administration of said one or more REMA to a mammal modulates Rev-erbα expression, activity, and/or subcellular location in at least a portion of the mammal's hepatic stellate cells (HSCs) wherein the one or more REMA comprises 1,1-Dimethylethyl N-[(4-chlorophenyl)methyl]-N-[(5-nitro-2-thienyl)methyl])glycinate; N-Benzyl-N-(4-chlorobenzyl)-I-(5-nitrothiophen-2-yl) methanamine; N-Benzyl-N-(3,4-dichlorobenzyl)-I-(5-nitrothiophen-2-yl)methanamine; 2-((4-chlorobenzyl)((5-nitrothiophen-2-yl)methyl)amino)-N,N-dimethylacetamide; SR9009; SR9011; or combinations thereof, wherein the one or more REMAs is contained in a vector selected from the group consisting of a plasmid, cosmid, phagemid, or virus.

26. The composition of claim 25, wherein said therapeutically effective amount of said one or more REMA comprises a quantity sufficient to modulate at least one of Rev-Erbα expression in a mammal, halt activation of HSCs in a mammal, or revert at least a portion of any activated HSCs into a quiescent phenotype in a mammal.

27. The composition of claim 25, wherein the one or more REMA is linked to a carrier/targeting moiety.

28. The composition of claim 25, wherein the composition is provided in a form selected from a liquid injectable composition, a tablet, a capsule, loaded nanoparticle, an orally administrable liquid, or a transdermal patch.

* * * * *